(12) United States Patent
Palmskog et al.

(10) Patent No.: US 10,520,439 B2
(45) Date of Patent: Dec. 31, 2019

(54) SYSTEM AND METHOD FOR DRUG DETECTION IN EXHALED BREATH (75) Inventors: Göran Palmskog, Järfälla (SE); Olof Beck, Saltsjöö-Boo (SE)

(73) Assignee: Sensa Bues AB, Sollentuna (SE)

( * ) Notice: Subject to any disclaimer, the term of this patent is extended or adjusted under 35 U.S.C. 154(b) by 462 days.

(21) Appl. No.: 13/394,609

(22) PCT Filed: Sep. 9, 2010

(86) PCT No.: PCT/EP2010/063266
§ 371 (c)(1),
(2), (4) Date: May 29, 2012

(87) PCT Pub. No.: WO2011/029889
PCT Pub. Date: Mar. 17, 2011

(65) Prior Publication Data
US 2012/0302907 A1 Nov. 29, 2012

Related U.S. Application Data

(60) Provisional application No. 61/240,752, filed on Sep. 9, 2009.

(51) Int. Cl.
*A61B 5/08* (2006.01)
*G01N 21/65* (2006.01)
(Continued)

(52) U.S. Cl.
CPC ........... *G01N 21/658* (2013.01); *A61B 5/082* (2013.01); *A61B 5/412* (2013.01); *G01J 3/44* (2013.01); *G01N 33/497* (2013.01)

(58) Field of Classification Search
CPC ................................. A61B 5/082; A61B 5/097
(Continued)

(56) References Cited

U.S. PATENT DOCUMENTS

| 4,292,978 A | 10/1981 | Guth |
| 4,809,810 A * | 3/1989 | Elfman ............... G01N 33/4972 180/272 |

(Continued)

FOREIGN PATENT DOCUMENTS

| DE | 19718924 A1 | 10/1998 |
| EP | 0997733 A2 | 5/2000 |

(Continued)

OTHER PUBLICATIONS

Office Action dated Oct. 21, 2013 in connection with related Japan Application No. Tokugan-2012-528364.

(Continued)

*Primary Examiner* — Etsub D Berhanu
(74) *Attorney, Agent, or Firm* — Downs Rachlin Martin PLLC (57) ABSTRACT

A portable system (10) is disclosed for collecting a sample from exhaled breath of a subject. Drug substance in the exhaled breath are detected or determined. The sample is collected for further analysis using mass-spectroscopy. The system comprises a sampling unit (14) and a housing (12) arranged to hold the sampling unit (14), the sampling unit (14) is adapted to collect non-volatile and volatile compounds of the at least one drug substance from the exhaled breath from the subject. The housing (12) has at least one inlet (15) for the subject to exhale into the housing (12) to the sampling unit (14) and at least one outlet (16) for the exhaled breath to exit through.

24 Claims, 7 Drawing Sheets (51) Int. Cl.
 *G01J 3/44* (2006.01)
 *A61B 5/00* (2006.01)
 *G01N 33/497* (2006.01)

(58) Field of Classification Search
 USPC ........................................................ 600/532
 See application file for complete search history.

(56) References Cited

U.S. PATENT DOCUMENTS

| | | | |
|---|---|---|---|
| 5,042,501 | A | 8/1991 | Kenny et al. |
| 5,195,527 | A | 3/1993 | Hicks |
| 5,465,728 | A | 11/1995 | Phillips |
| 5,467,776 | A | 11/1995 | Hamilton |
| 5,478,377 | A | 12/1995 | Scavnicky et al. |
| 5,518,002 | A * | 5/1996 | Wolf ............... A61B 5/0878 482/13 |
| 5,721,102 | A | 2/1998 | Vo-Dinh |
| 5,834,626 | A | 11/1998 | De Castro |
| 6,097,480 | A | 8/2000 | Kaplan |
| 6,209,541 | B1 | 4/2001 | Wallace |
| 6,409,806 | B1 * | 6/2002 | Jones ..................... B03C 3/28 128/205.29 |
| 6,623,997 | B2 | 9/2003 | Farquharson et al. |
| 7,450,227 | B2 | 11/2008 | Dwight et al. |
| 8,368,883 | B2 | 2/2013 | Palmskog et al. |
| 8,705,029 | B2 | 4/2014 | Palmskog et al. |
| 2002/0095078 | A1 | 7/2002 | Mannheimer et al. |
| 2002/0177232 | A1 | 11/2002 | Melker et al. |
| 2003/0000518 | A1 * | 1/2003 | Rabinowitz ............ A61K 9/007 128/200.14 |
| 2003/0004426 | A1 * | 1/2003 | Melker ................. G01N 29/022 600/532 |
| 2003/0028120 | A1 * | 2/2003 | Mault et al. .................. 600/531 |
| 2004/0236244 | A1 * | 11/2004 | Allen ..................... A61B 5/411 600/532 |
| 2005/0048660 | A1 * | 3/2005 | Bearer .......................... 436/132 |
| 2005/0051719 | A1 * | 3/2005 | Miller et al. .................. 250/287 |
| 2005/0065446 | A1 | 3/2005 | Talton |
| 2005/0137491 | A1 * | 6/2005 | Paz et al. ....................... 600/543 |
| 2005/0233459 | A1 * | 10/2005 | Melker .................. A61B 5/082 436/56 |
| 2006/0038990 | A1 | 2/2006 | Habib et al. |
| 2006/0078467 | A1 * | 4/2006 | Stock ................ G01N 33/0006 422/84 |
| 2006/0084182 | A1 | 4/2006 | Farquharson et al. |
| 2006/0119853 | A1 | 6/2006 | Baumberg et al. |
| 2006/0153740 | A1 | 7/2006 | Sultan et al. |
| 2006/0266353 | A1 | 11/2006 | Yamada et al. |
| 2007/0023627 | A1 * | 2/2007 | Finch et al. ................... 250/282 |
| 2007/0156211 | A1 * | 7/2007 | Ferren et al. .................. 607/101 |
| 2007/0185405 | A1 * | 8/2007 | Altobelli ............... A61B 5/082 600/529 |
| 2007/0224128 | A1 | 9/2007 | Dennis et al. |
| 2007/0252077 | A1 * | 11/2007 | Shoji ..................... B41J 2/471 250/234 |
| 2007/0258894 | A1 | 11/2007 | Melker et al. |
| 2008/0183388 | A1 | 7/2008 | Goodrich |
| 2009/0312662 | A1 * | 12/2009 | Colman ................. A61B 5/097 600/543 |
| 2011/0003396 | A1 * | 1/2011 | Jeppesen ............ C07D 495/22 436/110 |
| 2012/0212735 | A1 | 8/2012 | Palmskog et al. |
| 2013/0066223 | A1 | 3/2013 | Beck et al. |
| 2013/0128260 | A1 | 5/2013 | Palmskog et al. |
| 2014/0366609 | A1 | 12/2014 | Beck et al. |
| 2015/0033824 | A1 | 2/2015 | Hammarlund et al. |

FOREIGN PATENT DOCUMENTS

| | | | |
|---|---|---|---|
| EP | 2518499 | | 10/2012 |
| JP | H04507204 | | 12/1992 |
| JP | 2001-505660 | A | 4/2001 |
| JP | 2004-301749 | A | 10/2004 |
| JP | 2007-525670 | A | 9/2007 |
| JP | 2008102048 | | 1/2008 |
| JP | 2009-47593 | A | 3/2009 |
| WO | 0184112 | | 11/2001 |
| WO | 3057521 | A1 | 7/2003 |
| WO | 2005098429 | A2 | 10/2005 |
| WO | WO 2008092198 | A1 * | 8/2008 ............ A61B 5/097 |
| WO | 2009030957 | | 3/2009 |
| WO | 2009045163 | A1 | 4/2009 |
| WO | 2011029888 | A1 | 3/2011 |

OTHER PUBLICATIONS

Sagmuller et al., Application of SERS spectroscopy to the identification of (3,4-methylenedioxy)amphetamine in forensic samples utilizing matrix stabilized silver halides, Analyst, Royal Society of Chemistry, GB, vol. 126, No. 11, Nov. 1, 2001, pp. 2066-2071.

Sulk et al., Surface-Enhanced Raman Scattering Detection of Amphetamine and methamphetamine by Modification with 2-Mercaptonicotinic Acid, Applied Spectroscopy, the Society for Applied Spectroscopy, Baltimore, US, vol. 53, No. 8, Jan. 1, 1999, pp. 954-959.

European Search Report dated Jun. 8, 2011, in connection with related EP Application No. 11157565.

Written Opinion dated Jun. 8, 2011, in connection with related EP Application No. 11157565.

Extended European Search Report dated Apr. 11, 2012, in connection with related EP Application No. 12 15 8911.

Written Opinion dated Apr. 11, 2012, in connection with related EP Application No. 12 15 8911.

Marks, P, "Taking on the drugged and drunk drivers," New Scientist, Reed Business Information, Surrey, GB, vol. 188, No. 2528, Dec. 3, 2005, pp. 28-29.

Beck, Olof et al., Amphetamines Detected in Exhaled Breath from Drug Addicts: A New Possible Method for Drugs-of-Abuse Testing; Journal of Analytical Toxicology, vol. 34 Jun. 2010; pp. 233-237.

Zwir-Ferenc, A., et al., Solid Phase Extraction Technique—Trends, Opportunities and Applications; Polish J. of Environ. Stud., vol. 15, No. 5 (2006); pp. 677-690.

EPO Communication re Personal Consultation with Examiner, dated Dec. 10, 2012, issued in connection with related EP10751947.2.

EPO Communication, Article 94(3) dated Oct. 23, 2012, issued in connection with related EP10751947.2.

EPO Communication, Article 94(3) dated Mar. 7, 2013, issued in connection with related EP10751947.2.

Sanchez, C et al., "Determination of Nitroaromatic Compounds in Air Samples at Femtogram Level Using C18 Membrane Sampling and On-line Extraction with LC-MS," Analytical Chemistry, Sep. 1, 2003, pp. 4639-4645, vol. 75, No. 17.

Buszewski Boguslaw et al., "Human exhaled air analytics: biomarkers of diseases," Biomedical Chromatography, Jun. 2007, pp. 553-566 & 588, vol. 21, No. 6.

Beck, O et al., "Method for determination of methadone in exhaled breath collected from subjects undergoing methadone maintenance treatment," Journal of Chromatography B: Biomedical Sciences & Applications, Elsevier, Amsterdam, NL., Jul. 3, 2010, pp. 2255-2259, vol. 878, No. 24.

Miekisch, W et al., "Assessment of propofol concentrations in human breath and blood by means of HS-SPME-GC MS," Clinica Chimica Acta, Elsevier BV, Amsterdam, NL, Sep. 1, 2008, pp. 32-37, vol. 395, No. 1-2.

International Search Report and Written Opinion dated Nov. 19, 2010, for related application PCT/EP2010/063266 filed Sep. 9, 2010, entitled "Drug Detection in Exhaled Breath," Palskog, G et al.

Almstrand, Ann-Charlotte et al: "Airway monitoring by collection and mass spectrometric analysis of exhaled particles", Analytical Chemistry, American Chemical Society, vol. 81, No. 2, Jan. 15, 2009, pp. 662-668, XP007915715; ISSN: 0003-2700.

Beck, Olof et al., "Study on the sampling of methadone from exhaled breath", Journal of Analytical Toxicology, vol. 35, No. 5, Jun. 2011, pp. 257-263, XP55045425.

(56) References Cited

OTHER PUBLICATIONS

Beck, Olof et al., "Demonstration that methadone is being present in the exhaled breath aerosol fraction", Aug. 3, 2011, Journal of Pharmaceutical and Biomedical Analysis, pp. 1024-1028, ISSN: 0731-7085.
Bernd Sagmuller et al, Application of SERS Spectroscopy to the identification of (3,4-methylenedioxy) Amphetamine in Forensic Samples Utilizing Matrix Stabilized Silver Halides, Oct. 2001, pp. 2066-2071, vol. 126, No. 11, The Analyst, The Royal Society of Chemistry 2001.
Fabian, Patricia et al., "Influenza virus in human exhaled breath: an observational study", PLOS One 2008, vol. 3, No. 7, Jul. 16, 2008, p. e2691, XP7921865, ISSN: 1932-6203.
International Preliminary Report on Patentability dated Oct. 27, 2011, in connection with related PCT/EP2010/063265 filed Sep. 9, 2010.
International Search Report dated Nov. 24, 2010, in connection with related PCT/EP2010/063265 filed Sep. 9, 2010.
International Search Report dated May 23, 2013, in connection with related PCT/EP2013/054789, filed Mar. 8, 2013.
International Search Report dated Oct. 4, 2013, in connection with related PCT/EP2013/068860, filed Sep. 11, 2013.
Mutlu G. M., et al., "Collection and analysis of exhaled breath condensate in Humans", American Journal of Respiratory and Critical Care Medicine, American Lung Association, NY, NY, vol. 164, 2001, pp. 731-737, XP003012811, ISSN: 1073-449X.
Written Opinion dated May 23, 2013, in connection with related PCT/EP2013/054789, filed Mar. 8, 2013.
Written Opinion dated Oct. 4, 2013, in connection with related PCT/EP2013/068860, filed Sep. 11, 2013.
Office Action dated Aug. 2, 2013, in connection with related U.S. Appl. No. 13/739,607, filed Jan. 11, 2013.
Response to Office Action dated Dec. 2, 2013, in connection with related U.S. Appl. No. 13/739,607, filed Jan. 11, 2013.
Office Action dated Aug. 13, 2014, in connection with related U.S. Appl. No. 13/416,956, filed Mar. 9, 2012.
Response to Office Action dated Jan. 13, 2015, in connection with related U.S. Appl. No. 13/416,956, filed Mar. 9, 2012.
International Search Report dated Apr. 2, 2012, issued in connection with related PCT/EP2012/054180, filed: Mar. 9, 2012.
Written Opinion dated Apr. 2, 2012, issued in connection with related PCT/EP2012/054180, filed: Mar. 9, 2012.
Periago, J. F. et al.; "Design and evaluation of an exhaled breath sampler for biological monitoring of organic solvents," Journal of Applied Toxicology, vol. 12, No. 2, Apr. 1, 1992; pp. 91-96; ISSN: 0260-437X.
European Search Report dated Jul. 3, 2014 in connection with related EP14164314.8, filed Sep. 9, 2010.
Written Opinion dated Jul. 3, 2014 in connection with related EP14164314.8, filed Sep. 9, 2010.
Office Action dated Dec. 17, 2015, in connection with U.S. Appl. No. 14/222,696, filed Mar. 24, 2014.
Advisory Action dated Jul. 24, 2015, in connection with related U.S. Appl. No. 13/416,956, filed Mar. 9, 2012.
Response to Final Office Action dated Jun. 29, 2015, in connection with related U.S. Appl. No. 13/416,956, filed Mar. 9, 2012.
Final Office Action dated Apr. 28, 2015, in connection with related U.S. Appl. No. 13/416,956, filed Mar. 9, 2012.
Response to Office Action dated Oct. 28, 2015, in connection with U.S. Appl. No. 13/416,956, filed Mar. 9, 2012.
Office Action dated Jan. 7, 2016, in connection with U.S. Appl. No. 14/427,229, filed Mar. 10, 2015.
Response to Office Action dated Jun. 1, 2016, in connection with U.S. Appl. No. 13/416,956, filed Mar. 9, 2012, Olof Beck.
Amendment and Response to First Non-Final Office Action dated Apr. 18, 2016, in connection with U.S. Appl. No. 14/222,696, Palmskog et al.
Final Office Action dated Jun. 15, 2016, in connection with U.S. Appl. No. 14/222,696, Palmskog.
Amendment and Response to First Office Action dated Apr. 6, 2016, in connection with U.S. Appl. No. 14/427,229, Beck.
Notice of Allowance dated Apr. 26, 2016, in connection with U.S. Appl. No. 14/427,229, Beck.
Office Action dated Feb. 1, 2016 related to U.S. Appl. No. 13/416,956, filed Mar. 9, 2012, Olof Beck.

\* cited by examiner

SYSTEM AND METHOD FOR DRUG DETECTION IN EXHALED BREATH

FIELD OF THE INVENTION

This invention pertains in general to the field of systems and methods for collecting a sample from exhaled breath of a subject, and for detecting the presence or determining the quantitative amount of at least one drug substance in said exhaled breath. More particularly the invention relates to such portable systems.

BACKGROUND OF THE INVENTION

It is known that exhaled breath is commonly used in alcohol testing and today's technology makes it possible to perform on-site breath testing with legally defensible results using infrared spectroscopy.

Testing for other illicit drugs of abuse traditionally requires blood or urine samples. Alternatively specimens comprising hair, sweat or oral fluid could be used. Blood sampling is invasive and requires medically trained personnel, why test subject often have to be transported to a hospital for sampling. This is time and effort consuming. With long lead times the test result will be too old. Urine sampling is considered intruding on personal integrity. Even other issues related to samples and specimens taken from a subject to be tested arise. For instance for blood samples, and especially for urine samples are at risk of the subject exchanging the samples or using clean samples from another subject to avoid being discovered with traces of illicit drugs.

Thus, there is a need to provide a non-invasive, not-specimen based apparatus, system and/or method for detecting the presence or determining the quantitative amount of at least one drug substance in a subject.

Hence, an improved apparatus, system and/or method for on-site sampling of a subject for drug substances is desired. Such an apparatus, system and/or method for sampling the subject for illicit drugs of abuse and/or medical drugs would be desired. The apparatus, system and/or method should be efficient, non-bulky, user friendly both for operators and the subject. It should further be not intruding and not invasive.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a system and a method, according to the appended patent claims.

According to one aspect of the invention, a portable system is provided that is configured to collect a sample from exhaled breath of a subject, and for detecting the presence or determining the quantitative amount of at least one drug substance in said exhaled breath.

The invented system is adapted to collect the sample for further analysis using mass-spectroscopy. The system comprises a sampling unit and a housing arranged to hold the sampling unit. The sampling unit is adapted to collect non-volatile and volatile organic compounds of the at least one drug substance from the exhaled breath from the subject. The housing comprises at least one inlet for the subject to exhale into the housing to the sampling unit and at least one outlet for the exhaled breath to exit through.

The exhaled breath volume is not stored in a volume for analysis of the chemical contents of the entire breath volume. Rather, traces of the drug substance are attached to a collecting element and then further analyzed from this element. Analysis is not made online of the breath volume, but of the traces in the collecting element. The collecting element may be removable from a housing and sent further for the analysis. Collection of the traces is made quick, a single exhalation may be sufficient. Less than 10 subsequent exhalations are more than sufficient to obtain reliable results and improve robustness of the system. This is far more convenient and quicker than any previous breath sample collection methods.

Compounds exhaled in expired air may originate from blood by a mechanism of producing a gas phase in the alveoli. Alternatively, compounds may originate from other parts of the airways. Non-volatile and volatile compounds are transferred from the lungs, possibly carried by an aerosol. Here the non-volatile and the volatile compounds are drug substances and could be either medical drugs or legal or illegal narcotic substances. The drug substances are collected on-site using a portable system comprising a sampling unit. The collected samples could be sent to a laboratory for further analysis. Alternatively, compact on-site analysis may be performed. The analysis is performed using a suitable analyzing method like spectroscopy or preferably mass-spectroscopy. The sampling unit could either be a suitable element for collecting the non-volatile compounds or be a sampling unit comprising an element that is suitable to collect both non-volatile and volatile compounds.

Since the system is small and designed to be easy to handle it can be used by any personnel on-site. Thus the system is adapted to be used instead of more intrusive tests like tests based on the much common urine or blood samples.

The housing could be made of any material like, plastic, metal or glass as long as it is possibly to clean or make the housing aseptic. The housing could alternatively or in addition be made of a disposable material. In this way the housing may, after being used for sampling, and for some embodiments also as part of the analyze step, be discarded.

Some embodiments of the invention comprise a detachable mouthpiece element connectable to the inlet and being in communication with said housing element.

The detachable mouthpiece could be either a mouthpiece similar to the mouthpieces used by alcoholic test or a mask or any other type of mouthpieces suitable for exhaling through. The mouthpiece could be fitted with valves or flow sensors. The valve could be used to separate inspired fro expired air and also serve as a saliva trap. The mouthpiece could be used either for making the inhalation into the portable system easier or for sanitation when the system is not a disposable system and therefore needs to be cleaned between use.

In one embodiment of the portable system the housing is a Solid-phase extraction (SPE) cartridge or a SPE-column. The housing could also, in some embodiments be a modified type of sorbent tube to make it suitably to exhale through.

The SPE-cartridge or SPE-column could be used as a housing comprising the sampling element or as part of or a sampling unit covered by a housing. The SPE-cartridge could, after being used for sampling exhaled breath, be directly placed on a manifold for extracting the drug substances from the SPE-cartridge. Hence this provides for making the workflow easier and smoother since the amount of steps during the analysis will be reduced. The risk for contaminating the sample during the handling will therefore be reduced. The sorbent tube could be used in a similar fashion as SPE-cartridge/column.

To make it easy to exhale through the SPE-cartridge the cartridge could be modified with for example larger inlets and outlets. In one embodiment of the invention the subject exhales directly into the SPE-cartridge/column or the sorbent tube and the whole cartridge or sorbent tube (being a portable system) could be sent to the laboratory to be analyzed.

In another embodiment of the invention, the portable system could comprise a pump arranged downstream the sampling unit.

The pump could be placed after the housing element and before or after at least one outlet. The pump is arranged for helping the subject to pass the exhaled breath through the portable system.

This breathing assistance could benefit and help test subjects that have a low or reduced breathing capacity.

In yet another embodiment of the invention, the portable system has a pressure drop through the system not higher than 2 cm water. To be able to collect exhaled breath samples from most subjects the pressure drop through the system has to be as low as possible. 2 cm water is what a person diagnosed with Chronic obstructive pulmonary disease (COPD) can breath through.

In some embodiments of the invention, the sampling unit comprises at least one filter membrane. The filter membrane has preferably a mesh size to collect particles from the exhaled breath with a size of 0.2-0.7 µm. And even more preferably is the filter membrane chosen such that a pressure drop of less than 2 cm water occurs between said inlet and outlet at an exhalation flow rate of over 0 and up to 9 liters per second.

The flow rate of a subject's exhalation depends on some parameters for example the subject's age, mental state (MR, Alzheimer's), medical condition (sepsis, Parkinson's) or other medications like benzodiazepines, opiates, neuroleptics, local anesthetics or intoxicants etc.

The filter membrane could, after the subject has exhaled through the system, easily be removed and sent to a laboratory to be analyzed. The portable system could then be cleaned and a new filter could be put in place. The filter membrane could also be directly placed inside the aforementioned SPE-cartridge that is either used as a housing or as part of or a sampling unit inside a housing.

In embodiments of the invention the collected particles from the filter are analyzable by mass-spectroscopy.

The mass-spectroscopy is the preferred method, also for other embodiments than those comprising a filter in the sampling unit, since the technology has a very high selectivity and sensibility of bioanalysis especially with regards to trace analytes in biological samples. The preferable interface is liquid chromatography.

In another embodiment of the invention, is the filter membrane an electrostatic filter membrane.

An electrostatic filter is here defined as a filter that has an electrostatic charge that has a polarity opposite the particles that should be collected from the exhaled breath.

The filter could be made highly selective to certain drug substances.

In a further embodiment of the invention is the filters emptied from collected particles and analyzed by dissolving the collected particles from the exhaled breath in a solvent and placing the solution on a Surface Enhanced Raman Spectroscopy (SERS)-substrate to be analyzed using Raman spectroscopy. The analysis could also be performed using a SERS-sensor such as a SERS-probe.

In one embodiment of the invention is the at least one filter membrane at least two filter membranes to discriminate at least two different drug substances. This is provided by having filter membranes with different filter selectivity.

This may be provided by stacking or arranging at least two filters adjacent each other. Each filter may have different mesh types or electrostatic charges. The sampling unit could thus discriminate between at least two different drug substances. This could improve the analysis.

In an embodiment, the sampling unit comprises at least one solid-phase microextraction (SPME)-cartridge to be further analyzed using gas chromatography-mass spectroscopy GC-MS.

The SPME-cartridge is a hollow fiber that is arranged such that it will trap the exhaled drug substances. The SPME-cartridge could then be analyzed directly using GC-MS.

In some embodiments of the invention the portable system comprises a compartment for collecting saliva and/or condensate. The compartment could be arranged between the at least one inlet and the sampling unit and/or after the sampling unit and the at least one outlet. This may prevent clogging of the sampling unit, e.g. when having hydrophobic filters that may become saturated by condensed humidity or saliva from the exhaled breaths.

By arranging the sampling unit inside the housing so that the housing becomes divided, two spaces could be formed: one space between the at least one inlet and the sampling unit and one space between the sampling unit and the at least one outlet. By arranging a compartment communicating to the space between the at least one inlet and the sampling unit saliva and/or condensate formed, from the moist in the exhaled breath, on the walls of the housing and on the sampling unit can be collected. A similar compartment capable to collect condensate could be arrange communicating with the space after the sampling unit and the at least on outlet.

This could help to avoid the sampling unit to be saturated due to becoming wet by saliva, moist and/or condensate.

The compositions of the exhaled particles are believed to reflect the airway liquid fluid, which probably reflects the blood content of the drug. The drug substances are believed by the inventors to most likely to come from the central part of the airway system. The non-volatile drug substances are carried as liquid droplets (aerosol) that are formed during normal breathing by the turbulent airflow causing the airway-lining fluid to nebulize. The aerosols are possible to collect as exhaled breath condensates. The theory comes from Anesthetic studies that have showed that Anesthetic potency correlates with lipid solubility. Holds true across species and implies when a specific hydrophobic region is occupied the more soluble the anesthetic agent is in blood the faster the drug goes into the body. The drug substances could also be volatile as part of the exhaled breath.

In an embodiment of the invention, is the detectable drug substance including in the noncomprehensive list comprising Amphetamines, ecstasy, Cannabis (THC and cannabinoids), Opiates heroin/morphine, 6-AM), Cocaine, Benzodiazepines, Propoxyphene, Methadone, Buprenorphine, Tramadol, LSD, Designer/Internet drugs, Kathinon, GHB, Meprobamat, Z-drugs, Tryptamines, Anabolic steroids, Alcohol/markers but are not limited to these since other illicit drugs not included in the list could should also be detectable due to similar interchanges with the human body as the above mentioned illicit drug substances.

According to another aspect of the invention, a method is provided, for portably collecting a sample from exhaled breath of a subject, and for detecting the presence or determining the quantitative amount of at least one drug substance in the exhaled breath. The method comprises collecting the sample using a system, according to the aforementioned aspect of the invention, from the subject; and analyzing the collected non-volatile and volatile compounds of the at least one drug substance using mass-spectroscopy.

In another embodiment of the method the collecting comprises collecting non-volatile and volatile compounds of the at least one drug substance from the exhaled breath from the subject in a sampling unit held in a housing of the system.

In another embodiment of the method, the collecting comprising the subject exhaling into at least one inlet of the housing to the sampling unit and further to at least one outlet to exit from the housing.

In another embodiment, the method comprises discriminating between at least two different drug substances by means of at least two sampling elements.

The sampling element is defined as an element for suitably collecting the drug substances. This could either be the sampling unit itself or a collecting element, such as a filter or fiber probe tip, arranged in the sampling unit.

In an embodiment, the method comprises collecting the at least one drug substance using at least one filter membrane arranged in the sampling unit.

In an embodiment, the method comprises collecting the at least one drug substance using at least one SPME-cartridge arranged in said sampling unit.

Further embodiments of the invention are defined in the dependent claims, wherein features for the second and subsequent aspects of the invention are as for the first aspect mutatis mutandis.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1:
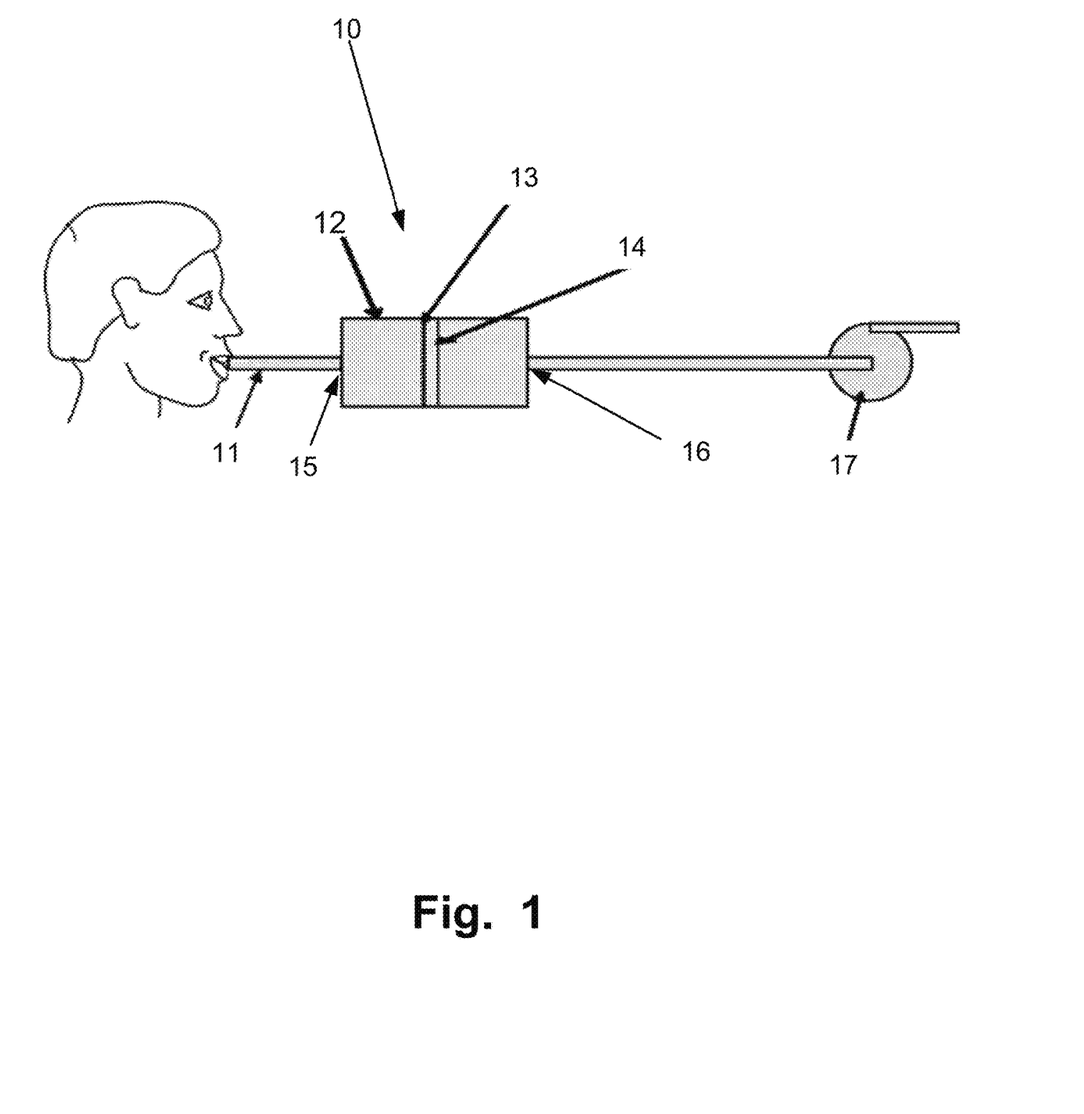
FIG. 1 is a schematic illustration that shows an embodiment of a portable system configured to collect a sample from exhaled breath of a subject.

In an embodiment of the invention according to FIG. 1 a portable sampling system 10 is shown. The system comprises a housing 12 for holding the sampling unit 14. The housing 12 could either be one sole element or be constructed out of two or more parts. The housing could be made of any material or combinations thereof such as, metal, plastic, glass or ceramics.

The housing 12 comprises at least one inlet 15 that is designed to allow a subject to exhale in. The inlet is in one embodiment dimensioned to fit an optional mouth piece 11 preferably of the same size or type as a conventional mouth piece used for alcohol-test. The mouth piece 11 prevents contamination between subjects to sample.

The exhaled breath will then enter a first chamber of the housing that is designed to spread or focus the exhaled breath over or onto the sampling unit 14. The exhaled gas is thus conveyed in the housing 12 to the sampling unit 14 and brought into contact with the sampling unit 14.

The sampling unit comprises an arrangement that holds an element 13 for collecting at least one drug substance being non-volatile or volatile compounds from the volume of exhaled breath conveyed in the flow in the housing 12. It should be noted that the sampling unit 14 is not to be confused with an electronic sampling unit. The collecting element 13 is a physical entity on which the drug substance is collected. Collection may in different embodiments be based on various principles, singly or in combination, comprising depositing, catching, fastening, condensing of non-volatile and/or volatile constituents on the collecting element 13.

The element for collecting 13 the at least one drug substance is in some embodiments a filter membrane. Alternatively, or in addition, the collecting element 13 comprises an improved Solid phase micro-extraction (SPME)-cartridge. Alternatively, or in addition, the collecting element 13 comprises silica, polymers, imprinted polymers, or molecule imprinted polymers.

The selectivity of the collection element 13 can be controlled by the use of different types of collecting elements 13. When using silica (for example C4, C8 (hydrophilic) or C18 (hydrophobic) etc) either as a membrane, beads or gel, the selectivity depends on how hydrophobic the drug substances are. For polymers the collecting element is preferably highly crosslinked porous beads. These could be used to separate molecules depending on the size of the particle being filtered through the beads or how they bond with the surface of the polymers. The imprinted polymers such as molecular imprinted polymers are highly selective to a specific molecule or group of molecules with a size and shape being the same or similar to the cavities of the molecular imprinting. The cavities are made using a template and work as a selective binding sites.

The at least one drug substance may comprise one or more drug compounds.

To allow for a low pressure drop through the system 10 the outlet 16 is, in one embodiment of the invention, the whole back of the housing 12, which is the opening of the outlet 16. The filter is in this embodiment for instance attached to the housing 12 with retaining elements, such as clips. The filter may also be attached to the housing 12 by means of a second housing element, which may be a ring formed element that is either screwed or slid onto the first housing element retaining the filter. The filter itself will then form the back outlet opening 16 of the housing 12 while it is removable kept in the housing 12 by the retainer means.

In an embodiment, the second housing element, that is either screwed or slid onto the first housing element, comprises one central outlet 16. Alternatively, or in addition, many outlets 16 are arranged over the surface of the second outlet 16 in such a manner that the pressure drop is as low as possible when exhaling breath through the system 10.

In yet another embodiment the sampling unit 14 comprising the element suitably for collecting the drug substances 13 is hold in place by or made of spacer pieces attached to the walls of the housing 12 and either the sampling unit 14 or direct onto the element suitably for collecting the drug substances 13. Thus passages are created that will allow for a subject to easily exhale breath trough the portable sampling system 10.

In one embodiment, the sampling unit 14 is arranged such that there is an air passage around it so that the air can still flow through the sampling unit 14 even if the comprised filter (collecting element 13) became saturated causing an undesired high pressure drop. This kind of sampling unit 14 arrangement thus further improves the exhaled breath spreading inside the housing 12, whereby the surface of the sampling unit 12 is used more optimal.

In some embodiments the system 10 comprises a pump 17, arranged downstream the sampling unit 14, after the housing 12 and before or after at least one outlet 16 of the housing 12. The pump 17 is adapted to assists the subject to pass the exhaled breath through said system 10. The pump 17 generates a negative pressure over the sampling unit 14. For example if the subject has reduced lung capacity due to drug abuse or illness, this is advantageous. The sampling is assisted by the flow through the sampling unit 14 generated by the pump 17.

In some embodiments a flow sensor is arranged downstream the inlet 15. The sensor could be arranged for measuring an exhaled volume or flow of exhaled breath. The senor may be a differential pressure sensor for measuring the differential pressure across the sampling unit 14. The output from the differential pressure sensor is in non-turbulent flow linear to the flow through the sampling unit 14 with could be used to calculate the volume of exhaled breath having passed the sampling unit 14. This could then be used for calculation of the concentration of drug substances in the exhaled breath. Alternatively, or in addition, the volume data may be used for determining if sufficient volume has reached the sampling unit 14 for reliably determining the presence or the quantitative amount of a drug substance in the exhaled breath.

Some embodiments of the system 10 comprises at least one compartment for collecting saliva and/or condensate. The compartment could be arranged either between said at least one inlet 15 and said sampling unit 14 and/or after said sampling unit 14 and said at least one outlet 16. This would allow for saliva comprised in the exhaled breath or condensate formed, from the moist in the exhaled breath, on the sampling unit 14 to be collected and not affect the sampling unit 14 and the comprised collecting element 13 in any negative way. Negative ways could here be a wet or clogged sampling element 13 that collects the drug substances i.e. a filter membrane or a SPME-cartridge.

Figures 2A, 2B, 2C, 2D:
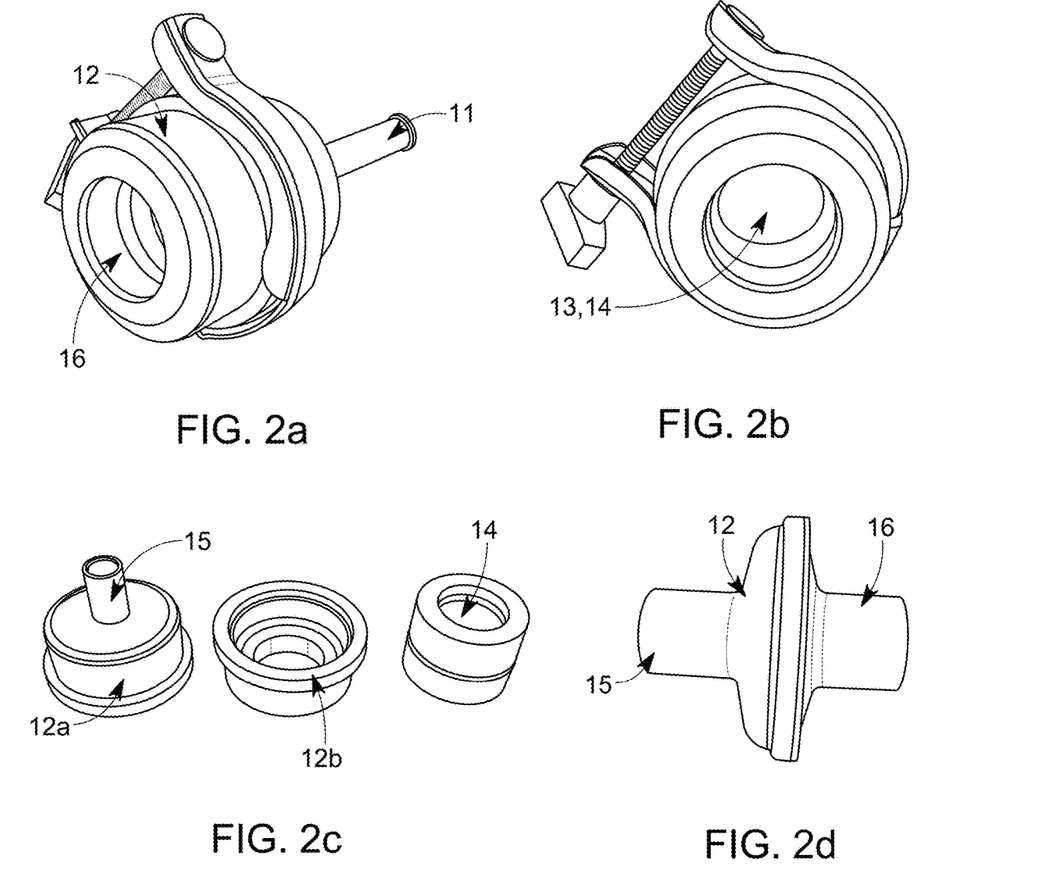
FIG. 2a-c is an embodiment showing a housing with the sampling unit comprising collecting element being a filter membrane.
FIG. 2d is an embodiment showing a housing with a sampling unit being a collecting element being a filter membrane.

FIG. 2a is an embodiment showing a housing 12 with a outlet 16 and an mouthpiece 11 in flow communication with an inlet. The outlet 16 covers the main portion of the back of the housing 12. In FIG. 2b can the sampling unit 14 comprising a collecting element 13, being a filter membrane, be seen through the outlet 16. FIG. 2c shows the main parts of this embodiment of the portable system 10; a first housing part 12a; a second housing part 12b; a sampling unit 14 comprising a filter membrane. The housing 12 is made of two parts the first part 12a comprises an inlet 15 that can be in flow communication with a mouthpiece 11 and a second part 12b with one large outlet 16.

FIG. 2d is an alternative or additional embodiment showing a housing 12 comprising a sampling unit being a filter membrane. This embodiment comprises two parts that when attached forms a housing 12 that holds a filter membrane. The housing comprises an inlet 15 suitable for a mouthpiece 11 and an outlet 16. This embodiment is very small, light weighted and easy to carry.

Figure 2E:
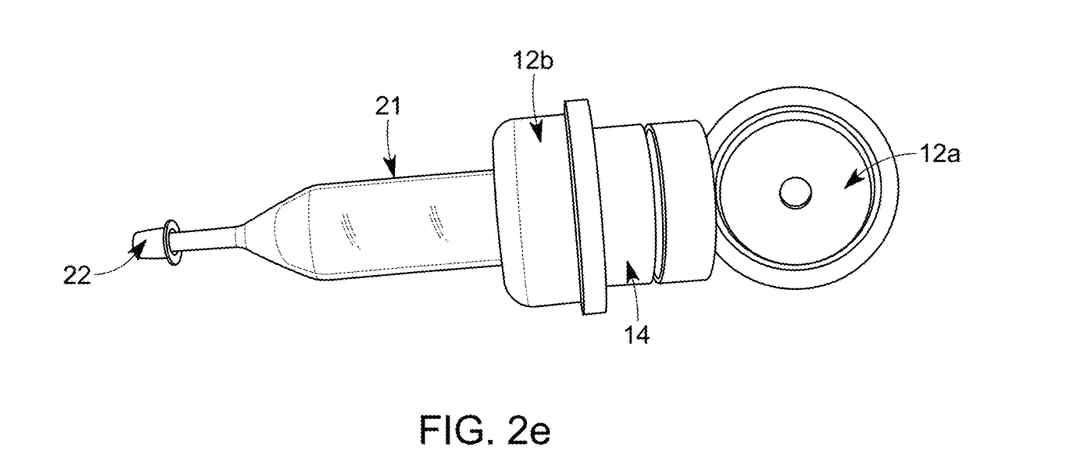
FIG. 2e is an embodiment showing a housing with a SPE-cartridge as part of a sampling unit.

FIG. 2e is a further embodiment showing a housing comprising two part 12a, 12b with a SPE-cartridge 21 as part of a sampling unit 14. The SPE-cartridge 21 comprising either silica beads, polymers or imprinted polymers for collecting the drug substance but could alternatively be fitted with a filter membrane. The SPE-cartridge 21 is seen sticking out through a outlet of the second part of the housing 12b and the bottom of the SPE-cartridge 22 works as the systems outlet for the exhaled breath. In a further embodiment of a similar portable system the housing is a modified SPE-cartridge. This means that the system can be made smaller than the system showed in FIG. 2e. After use, in both of the above cases, the whole SPE-cartridge 21 can be sealed and then sent to a laboratory where it could be directly placed on a manifold which will help to reduce the handling of the samples and at the same time reduce the possibilities of the sample to be contaminated.

Figure 3A:
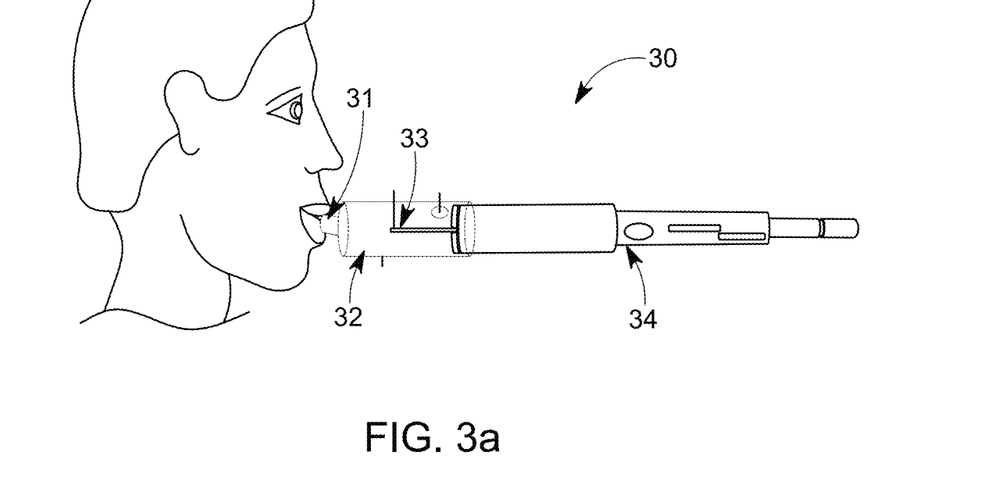
FIG. 3a is a schematic illustration that shows an embodiment of a portable system configured to collect a sample from exhaled breath of a subject wherein the sampling unit and the collecting element is a SPME-cartridge.
Figure 3B:
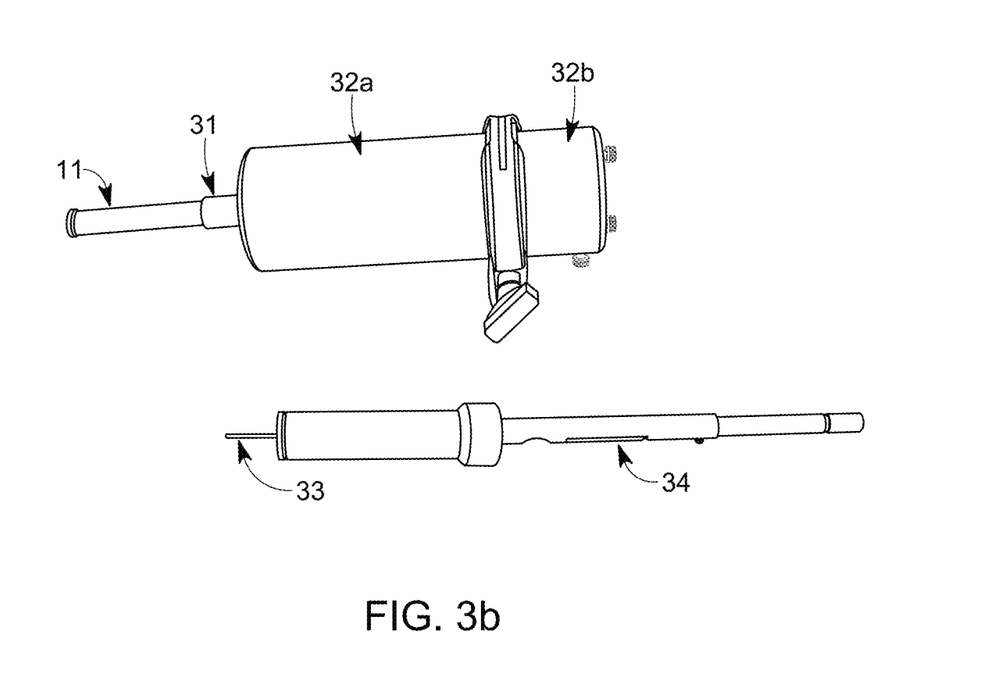
FIG. 3b is an embodiment showing a portable system configured to collect a sample from exhaled breath of a subject wherein the sampling unit and collecting element comprises a SPME-cartridge.

FIG. 3a is a schematic illustration that shows an embodiment of a portable system 30 configured to collect a sample from exhaled breath of a subject through an inlet 31 in flow communication with a housing 32. Wherein the sampling unit is a SPME-cartridge holder 34 and the collecting element is a SPME-cartridge 33. FIG. 3b shows a further embodiment of the portable system 30 configured to collect a sample from exhaled breath of a subject by means of a SPME-cartridge 33.

The system comprises a housing made of two part 32a and 32b. The first housing part 32a comprises with an inlet 31 in flow connection with a detachable mouthpiece 11. The housing comprises an outlet through which the SPME-cartridge holder 34 can be observed. In FIG. 3b the SPME-cartridge and the housing is shown as separate items.

Another embodiment, working similar to the described SPE-cartridge embodiment, is an embodiment wherein the sampling unit comprises a sorbent tube as the collecting element or wherein the sorbent tube is the sampling unit. Alternatively the sorbet unit, as for the SPE-cartridge case, could be the housing.

In the embodiments of the system 10 wherein a collecting element 13 is in form of a filter, the filter comprises a filtering membrane for the exhaled breath to diffuse through. The filter membrane is made of a suitable absorbing, yet gas permeable, material. The filter membrane will have a structure that catches and collects the drug substances being, exhaled particles, non-volatile or volatile compounds while letting gas pass through. Preferably the filter membrane is operable to sample or remove chemical compounds (drug substances) from the air with a high volumetric capacity while maintaining a low pressure drop across the filter substrate.

The filter membrane could also be an electrostatic filter in some embodiments.

The filter membrane may be of a nonwoven polymeric fibrous web that is transformed into an electret. The electret is a dielectric material exhibiting a quasi permanent electric charge. Electret filters usually loose their charge upon longterm use. However, in the present application, the filter will not be used extensive times. A single exhalation may be sufficient to collect sufficient traces for a reliable analysis. Therefore, loss of electric charge will not be a concern in implementations of electret filter embodiments.

The inventors believe that there could be different mechanisms that make it possible to use the filter membrane to collect the drug substances that could be either volatile organic compounds or non volatile organic compounds.

The filter membrane is preferable a layered filter membrane but could also be a single layer filter membrane.

The filter membrane may also be corrugated to enhance the filtering area within a given housing volume.

How the collecting of the analytes work is not entirely investigated. However, applicants believe that the first layer collects droplets by absorption or particles from exhaled breath. In addition, or alternatively, it could also be from exhaled breath absorbing or condensates and the small amount of water then evaporates, thus leaving thousands of analytes from the exhaled breath on the first surface. In addition, or alternatively, the analytes may be part of an aerosol conveyed by the exhaled breath, which aerosol particles stick to the first layer. Evaporation may also take place of aerosol, which then leaves the traces of the analytes on the first layer for analysis.

The first layer is gas permeable thus the analytes not collected on the first layer will pass through entering the second layer being a fiber like filter made of a synthetic, natural or half synthetic material. The second layer has a fiber density creating a surface volume. The gat will pass through the second layer that will collect the analytes by similar mechanism as described above but it could also be due to charges of the fibers that will make the analytes stick to the surface of the fibers.

The filter could also have layers of other materials such as silica, polymers, and/or imprinted polymers but could also be other types of materials that could collect analytes from exhaled breath.

In some embodiments, the filter material comprises glass fibers. The glass fibers may be bearing a permanent electrostatic charge to improve the efficiency of the filter in the current application. The glass fibers may be randomly oriented. The glass fibers may be held in place by suitable outer layers of a different material. The glass fibers may also be partly melt together to provide a solid filter cartridge. A highly efficient filter for collecting traces of chemical compounds from exhaled breath may thus be provided while maintaining a low pressure drop at high exhalation rates, as desired.

Due to the short time of usage, there is no risk of clogging the filters or reaching an increased pressure drop due to filter clogging.

Figure 4:
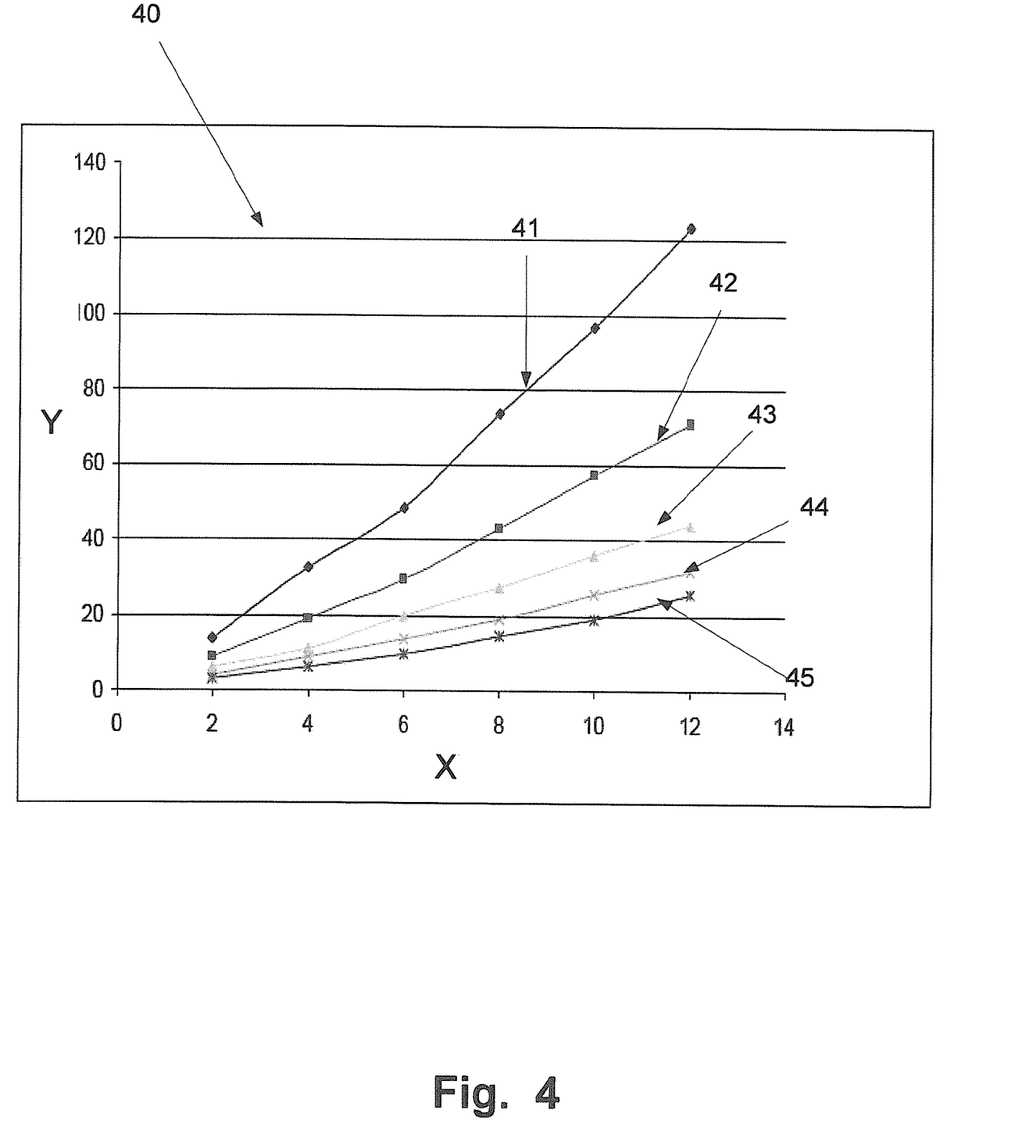
FIG. 4 is a graph that shows the pressure drop as a function of the gas-flow using the diameter of the filter as the parameter.

FIG. 4 is a graph 40 that shows the pressure drop in mm water Y as a function of the gas-flow X in the unit liter per minute and wherein the diameter of the filter is a parameter. The diameters of the filters tested are 10 mm (curve 41), 13 mm (curve 42), 16 mm (curve 43), 19 mm (curve 44) and 22 mm (curve 45).

When analyzing the filters, a small filter volume to extract from is preferred. This could be done, for this particular filter membrane, by making the diameter smaller. But at the same time the volume exhaled though the filter membrane should not generate a high drop of pressure. Preferably, the filter membrane should collect drug substances from a, as large volume of one deeply exhaled breath, as possible and at the same time not generate a high pressure drop. A healthy person should be able to handle a pressure drop of about 20 mm of water. According to FIG. 4 a filter size, for this particular filter membrane, of about 16 mm should be possible to use and still have an acceptable pressure drop. By modifying the physical or the chemical properties of the filter membrane or remove layers, smaller diameters may be possible.

The sensitivity of the used LC/MS method and this particular filter membrane makes it possible to detect drug substances from one exhaled breath.

Below is a table (table 3) showing results from a pre-study on five subjects at three different occasions. Here methadone (Mtd) in exhaled breath in pictogram per minute of exhalation is measured from the five subjects using three different collecting times, one collecting time at each occasion. All measurements were performed after the subject had their individual dose of methadone delivered to them.

TABLE 3

| Case no | Methadone dose (mg/d) | Mtd pg/min 1 min | Mtd pg/min 3 min | Mtd pg/min 10 min |
|---|---|---|---|---|
| 1 | 90 | 200 | 170 | 3840 |
| 2 | 120 | 50 | 40 | 27 |
| 3 | 100 | 10900 | 233 | 150 |
| 4 | 110 | 100 | 167 | 120 |
| 5 | 100 | 220 | 117 | 90 |

At the first occasion the subject exhaled for one minute, at the second occasion for three minutes and at the third occasion for 10 minutes. Except for subject number two who was not compliant and the exceptionally high values for subject number three and one at one of the occasions respectively, the results indicates that short collecting times are possible and even shorter collecting times should be performable using this particular filter membrane since the sensitivity of the LC-MS method allows for detections of lower amounts than the measured. The measured amount of drug substance could also be obtained by a small filter volume to extract from. This according to what previously have been described.

Figure 5:
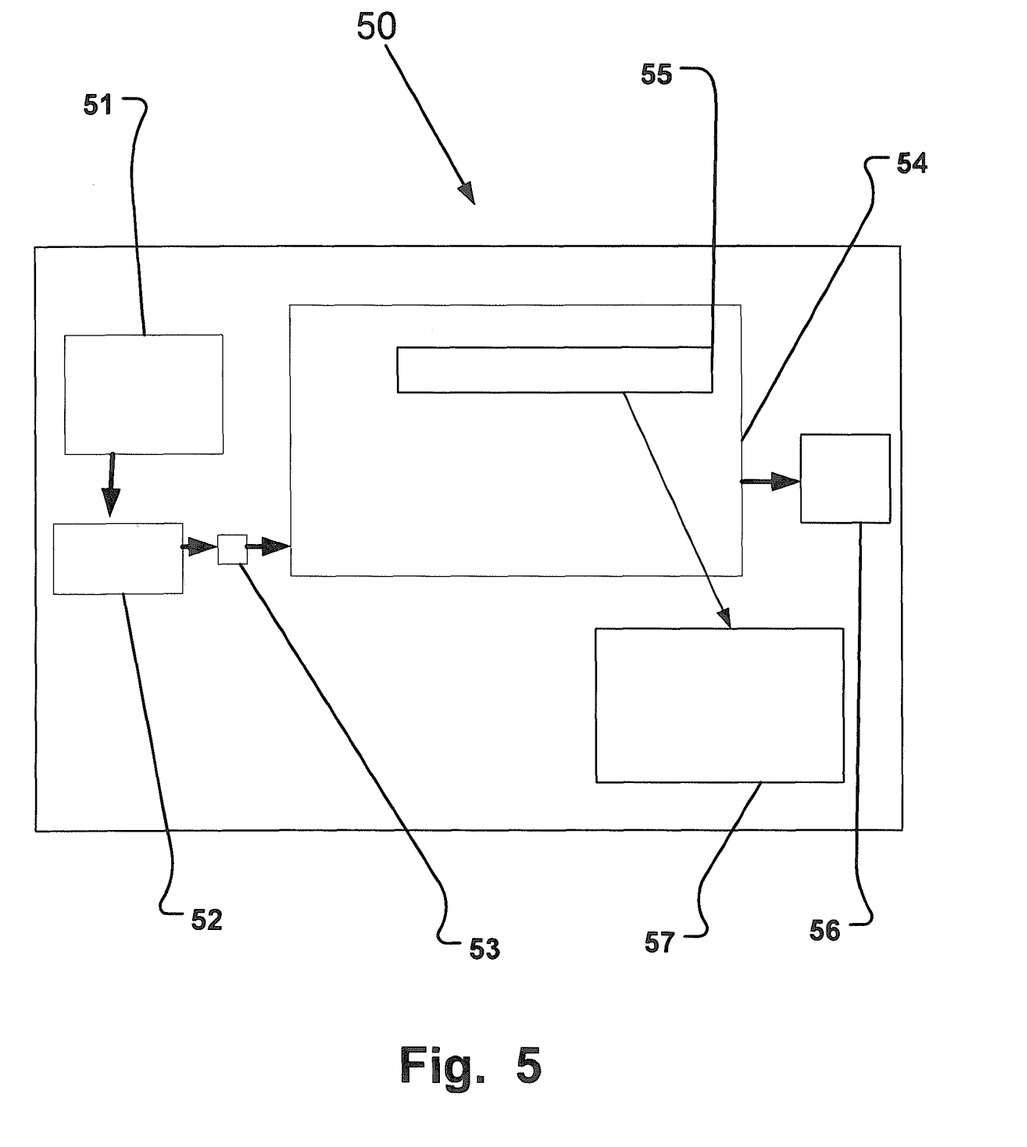
FIG. 5 is a schematic illustration illustrating an embodiment of a portable system configured to collect a sample from exhaled breath of a subject.

FIG. 5 is a schematic illustration illustrating an embodiment of a portable system 50 configured to collect a sample from exhaled breath of a subject 51. The subject will exhale through an optional mouthpiece 52 being in flow communication with a housing 54 via at least one inlet 53. The housing comprises a sampling unit 55 that could be either a collecting element or comprises a collecting element for collecting the drug substances from the exhaled breath. The exhaled breath exits the housing through at least one outlet 56. The sampling unit 55 and/or collecting element is sent to a laboratory 57 to be analyzed. In some embodiments of the portable system 50 the housing 54 could be the sampling unit 55.

The sampling unit 55 could comprise more than one collecting element, and/or the housing 54 could comprise more than one sampling unit, in any combination, suitably for collecting drug substances. This will make it possible to discriminate between different drug substances, thus making the analysis easier to perform. For example could the sampling unit 55 comprise at least one filter membrane and at least one SPME-cartridge. Another combination could include a stack of filter membranes with different physical and/or chemical properties. But multiple filter could also be used by using sampling unit 55 comprising areas fitted with different filter membranes.

The sampling system and elements for collecting drug substances should be kept clean and preferable be aseptic but do not need to be sterile.

Figure 6:
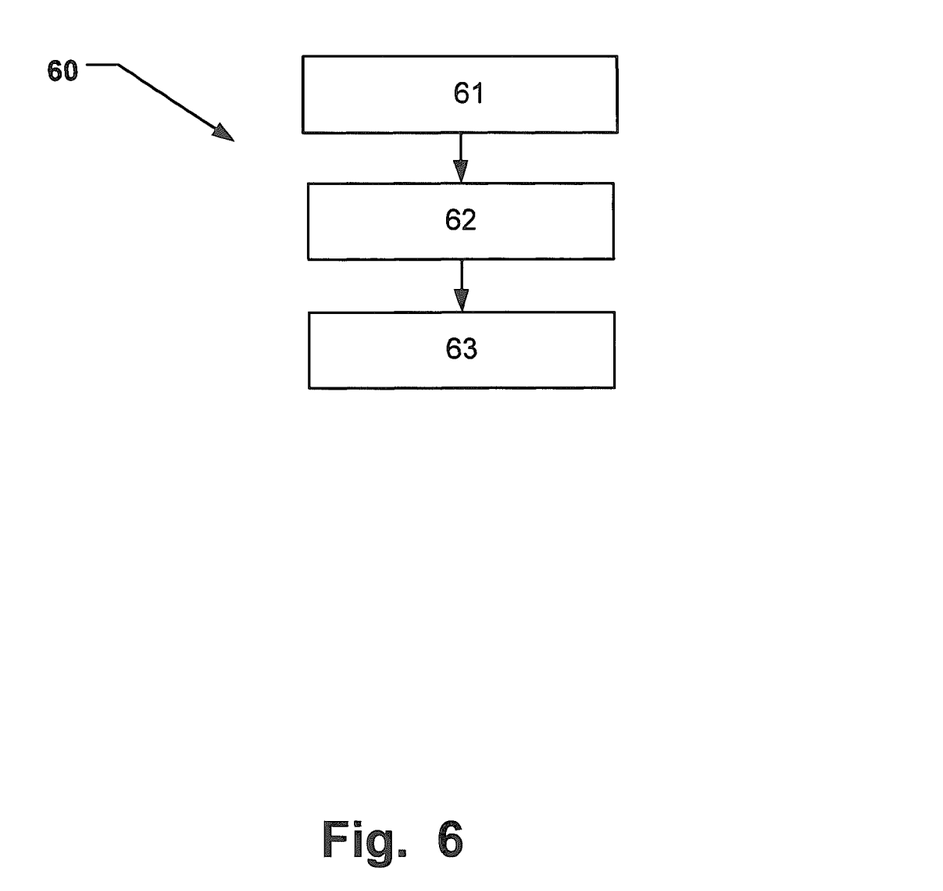
FIG. 6 is a flow-chart illustrating a method for using a portable system configured to collect a sample from exhaled breath of a subject.

FIG. 6 is a flow-chart illustrating a method 60 for using a portable system configured to collecting a sample 62 of exhaled breath and for detecting the presence or determining the quantitative amount 63 of at least one drug substance in the collected sample. The method comprises the steps of: A subject exhaling 61 into the invented portable system; a sampling unit will collect a sample 62 comprises drug substances; the collected sample will be analyzed using mass-spectroscopy 63.

Figure 7:
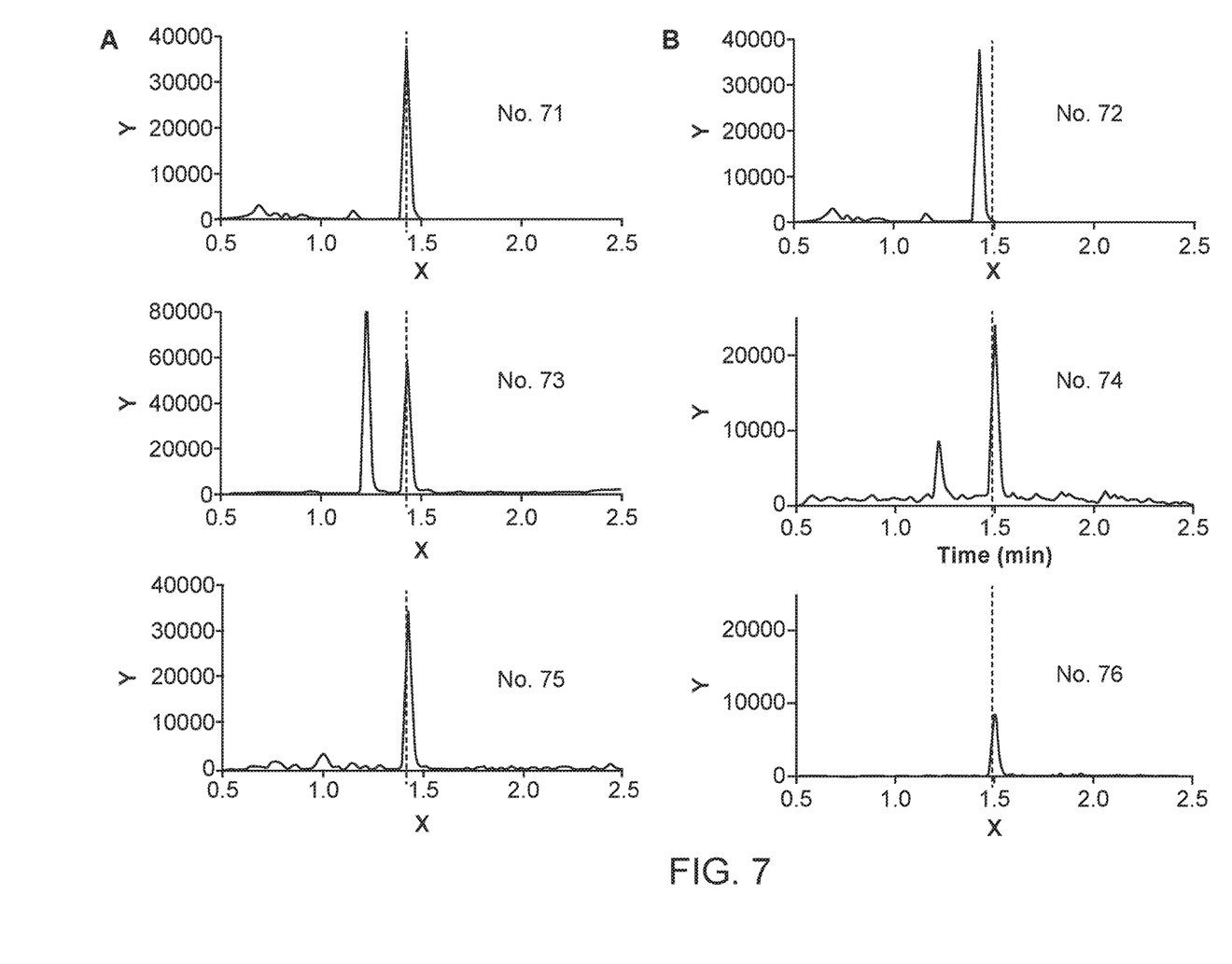
FIG. 7 shows a chromatogram indicating the presence of amphetamine and methamphetamine in exhaled breath.

In FIG. 7, chromatograms are shown from the identification of amphetamine (A) and methamphetamine (B) in exhaled breath from one subject after intake of "amphetamine". Y are here representing response (CPS) and X time (min). The conventionally analyzed urine and plasma data of the same subject taken for comparison reasons suggest possible intake of methamphetamine with amphetamine. Identification using a sampling unit and LC-MS-MS analysis was based on the presence of compounds with correct retention time and with correct relative abundance of two product ions. The identification of detected analytes was based on a correct relative (to amphetamine-$d_5$) retention time. Two product ions from the protonated molecules were monitored for amphetamine (m/z 136→119, Plot No. 75; 136→91, Plot No. 73) two for methamphetamine (m/z 150→119, Plot No. 76; 150→91, Plot No. 74). None of the control subjects without drug intake showed any of these peaks when analyzed from the implemented sampling unit. Thus, detection of amphetamine (A) and methamphetamine (B) in exhaled breath samples is reliably demonstrated. Further examples are given below.

With reference to FIG. 6 a flow-scheme is used to illustrate the invented method. A subject will exhale 61 in and out either for a certain time or for a fixed number of times such as 1 to 10 times into a portable system. When breathing a fixed number of times each exhale could be set to last for a fixed time. The exhalation could also be performed until a certain volume of exhaled breath has been obtained. A deep breath is preferred to reach exhaled breath from deep lying lung portions such as the central or the peripheral lung regions.

The exhaled breath will then be collected 62 by the sampling unit comprising at least one element suitably for collecting drug substances before it exits the system. The sampling unit will then be removed so that the at least one element suitably for collecting drug substances can be analyzed 63 using an appropriate mass-spectroscopy method. Alternatively, for some of the previously described embodiments, the whole housing could be sent to be analyzed.

In the following further examples of implementations of the invention and how an analysis may be performed is demonstrated. These original observations demonstrate drug testing based on sampling of expired air.

Example 1

Twelve patients reporting recent use of amphetamine (7 male, 5 female, ages 22-51) were recruited from two addiction treatment clinics in Stockholm (Beroendecentrum Stockholm). History of drug use was assessed by interview and by using two structured questionnaires, AUDIT (for alcohol) and DUDIT (for illicit drugs). The patients scored a median of 2.5 (range 0-34) in the AUDIT and 34.5 (range 12-43) in the DUDIT questionnaires. Recent drug intake was further investigated by analysis of blood plasma and urine samples. The urine and EDTA plasma samples were collected following the expired air sampling and stored at −80° C.

As control group eight drug-free healthy volunteers (3 male, 5 female, ages 29-67) were recruited. Compounds in expired air were collected by suction through an SPE cartridge (30 mg SPEC DAS, Varian, Lake Forest, Calif.). The patients were asked to breath in a face mask (no 1516, Intersurgical Ltd, Berkshire, UK) and a three way coupling was used to withdraw breath air. It was estimated that about half of the expired air was collected into the SPE cartridge via a 3 m long plastic tubing. Following sampling the SPE cartridge was stored at −80° C. and subsequently eluted with 2% ammonia (25%) in a mixture of methanol and ethyl acetate (20/80) at the time of analysis. The eluate was evaporated to dryness under nitrogen gas after addition of formic acid (10 μL of 10% formic acid in MeOH) and the residue was re-dissolved in 30 μL of 0.1% formic acid containing internal standard (5.94 ng amphetamined5).

An aliquot of 3 μL was subjected to analysis by SRM UPLC-MS/MS (Waters Quattro Premiere XE). The chromatographic system was a AQUITY UPLC BEH C18 column, 100 mm×1.0 mm, particle size 1.7 μm, with a gradient system with A=0.1% formic acid and B=acetonitrile. The linear gradient started at 100% A and ended at 70% A after 1.7 min. Thereafter 100% was pumped for 0.49 min before returning to 100% A.

Two product ions from the protonated molecules were monitored for amphetamine (m/z 136→119 75; 136→91 73), two for methamphetamine (m/z 150→119 76; 150→91 74) and one for amphetamine-d5 (m/z 141→124 71, 72) was done by selected reaction monitoring (SRM) in the positive electrospray mode, with 25 ms dwell time for each channel. The source block and desolvation temperatures were set at 150 and 350° C. respectively. Standards for quantification were prepared by using the matrix from blank SPE cartridges. Methods used for plasma and urine analysis were in routine use in the laboratory and based on LC-MS techniques.

In all 12 studied patients amphetamine and/or methamphetamine were detected in the expired air sample, which was in accordance with self-reported drug intake. In all cases the self reported intake was supported by analysis of blood plasma and urine. The presence and relative levels of amphetamine and methamphetamine indicated mixed drug use of both compounds, which is in accordance with a recent trend in Sweden observed in the clinical urine drug testing. In the 8 healthy controls no amphetamine or methamphetamine were detected.

Drug identification of detected analytes was based on a correct (relative to amphetamine-d5) retention time (±0.5%) and correct (<±20%) relative ion intensity ratio between the two product ions (FIG. 7). These criteria for identification are in accordance with scientific standards and are being successfully applied in urine drug testing. Since levels were generally low, background signal resulted in failure to fulfil identification criteria in some of the samples despite the fact that a signal was actually present. The amount of substance collected from expired air ranged from 0.2 to 103 pg/min for amphetamine and <0.3 to 139 pg/min for methamphetamine, see Table 1. No correlation between plasma and expired air levels was evident from the results. However, the sampling technique employed could not be validated for extraction efficiency. The SPE cartridge material is normally used for extraction of analytes from aqueous solutions. It is therefore unknown to what degree the amphetamines are trapped from expired air and the reproducibility of the extraction efficiency, which may have contributed to the variability in detected amounts in the expired air samples. Firm conclusions regarding correlation of expired air with blood levels were therefore not possible in this example. Using a flow meter as described above to determine the analyzed volume would provide an efficacy measure.

The urine and plasma data indicated that in most cases sampling was performed close to intake (<24 h), while in other cases low levels (<~5 μg/mL) in urine indicated longer times since intake (Table 1). Analytes were, however, still detected in the expired air. The relative proportion of amphetamine and methamphetamine in the expired air correlated well with plasma results, which further validates these findings.

Example 2

Thirteen patients undergoing methadone maintenance treatment (12 males, 1 female, ages 31-58) were recruited from the methadone program in Stockholm (Rosenlund, Stockholm). The patients were in steady-state and received supervised daily doses of methadone between 70 and 155 mg. The patients were subjected to constant control of compliance to treatment by urine drug testing. As a control group ten drug-free healthy volunteers (4 males, 6 females, ages 29-66) were recruited.

TABLE 1

| Case no | Self-reported drug use | Plasma* ng/mL | Urine* μg/mL | Expired air* pg/min |
|---|---|---|---|---|
| 1 | Amphetamine, diazepam | A = 166<br>M = 1.9 | A = 107<br>M = 0.69 | A = 0.7<br>M < 0.3 |
| 2 | Amphetamine, diazepam | A = 62.4<br>M = 0.6 | A = 14<br>M = 0.08 | A = 0.2<br>M < 0.3 |
| 3 | Amphetamine | A = 282<br>M = 2.1 | A = 30<br>M = 0.12 | A = 0.5<br>M < 0.3 |
| 4 | Amphetamine, methylphenidate | A = 110<br>M = 27 | A = 62<br>M = 5.4 | A = 19<br>M = 1.2 |
| 5 | Amphetamine, zopiclone | A = 52<br>M = 52 | A = 29<br>M = 19 | A = 0.4<br>M = 0.4 |
| 6 | Amphetamine, flunitrazepam, alprazolam, buprenorphine, morphine, zopiclone | No sample | A = 5.3<br>M = 62 | A = 103<br>M = 139 |
| 7 | Amphetamine | A = 4.3<br>M = 3.2 | A = 0.94<br>M = 0.40 | A < 0.6<br>M = 0.5 |
| 8 | Amphetamine, diazepam, methadone, heroin | No sample | A = 20<br>M = 119 | A < 0.3<br>M = 0.6 |
| 9 | Amphetamine, methylphenidate, alprazolam, diazepam | No sample | A = 6.7<br>M = 0.02 | A = 0.4<br>M < 0.3 |
| 10 | Amphetamine, flunitrazepam, methadone | A = 535<br>M = 64 | A = 229<br>M = 15 | A = 0.7<br>M < 0.3 |
| 11 | Amphetamine, clonazepam, methadone, cannabis | A = 504<br>M = 274 | A = 163<br>M = 51 | A = 5.3<br>M = 1.3 |
| 12 | Amphetamine, benzodiazepines, heroin, cannabis | A = 2.0<br>M = 0.1 | A = 1.3<br>M = 0.01 | A = 1.4<br>M = 0.3 |

*A = Amphetamine, M = methamphetamine

Sampling of Exhaled Breath

Compounds present in the exhaled breath were collected for 10 min by suction through a 47 mm Empore C18 disc (from 3M Inc.) using a membrane pump to assist the flow (about 300 mL/min). The subjects were asked to breathe more deeply than normal into a mouth piece (no. 4091148, Palmenco AB, Stockholm, Sweden) mounted in the sampling device holding the Empore disc (FIG. 1). It was estimated that all the exhaled breath was collected through the filter during the sampling period. Following sampling the Empore disc was dismantled using a tweezers and stored at −80° C. The sampling device was carefully cleaned between uses, which takes about 15 min.

Sample preparation: Following storage the Empore disc was cut into 5 mm×5 mm pieces using a scalpel and transferred to a 10 mL glass test-tube. A volume of 100 μL of 100 ng/mL methadone-d3 was added and mixed using a Vortex mixer, 300_L of 2-propanol was added (to wet the surface), mixed and finally 5 mL of 20% methanol in ethyl acetate was added. This mixture was shaken for one hour in a thermostatic bath at 37° C. Thereafter, the test-tube was centrifuged for 15 min at 3000×g at 10° C., the supernatant transferred to a new 10 mL glass test-tube, and the extraction procedure repeated using 1 mL of 20% methanol in ethyl acetate. Finally the two supernatants were combined, 10_L of 10% aqueous formic acid added and evaporated to dryness under a stream of nitrogen at a temperature of 40° C. The dry residue was dissolved in 100_L of 50% methanol in ethyl acetate.

Mass spectrometry analysis: An aliquot of 3 μL was subjected to analysis by UPLC-MS/MS (Waters Quattro Premier XE). The chromatographic system was a Aquity UPLC BEH C18 column, 100 mm×1.0 mm, particle size 1.7 μm, with a gradient system consisting of A=0.1% formic acid and B=acetonitrile. The mobile phase was 95% A for 1.2 min, followed by a linear gradient from 5% B to 65% B to 3.0 min. The equilibration time between injections was 4.0 min (95% A). The flow rate was 0.20 mL/min. Two product ions from the protonated molecules were monitored for methadone (m/z 310→265; 310→105) and one for methadone-d3 (m/z 313→268). This was done by SRM in the positive electrospray mode, with 75 ms dwell time for each channel. The minimum detectable amount (signal to noise 3) injected on column was about ~0.2 pg.

Quantification: Standards for quantification were prepared from fortified blank Empore discs. These were prepared by adding 10, 25, 50, 100 and 200 μL (corresponds to 3.0, 7.5, 15, 30 and 60 ng on the surface) of a solution containing 300 ng/mL of methadone. After drying the discs were prepared for analysis as described above. Calibration curves were constructed using linear regression analysis, with weighting factor 1/x.

Method validation: Five replications of the calibration curve were analyzed on different occasions. Limit of detection (LOD) and lower limit of quantification (LLOQ) was assessed by applying 10 pg of methadone onto a blank Empore disc and subject it for analysis. Imprecision and accuracy were estimated by analysis of six replicates of methadone applied on blank Empore discs at three levels (3.0, 15, 45 ng/disc). Recovery of extracting methadone from the Empore disc was estimated by comparison with a reference sample prepared directly in the final extract solvent. Matrix effects were estimated by extracting blank filter and filter from healthy volunteer and fortify with methadone in the final extract. This was compared with a reference sample without matrix. In addition, an infusion experiment was performed where injection of a control breath extract was injected while infusing methadone post-column and compared with injection of mobile phase A. The infusion rate was 10 µL/min and the infused methadone solution was 0.5 pg/mL in 0.1% formic acid in 50% methanol.

The peak area ratio of methadone to methadone-d3 was linear between 3 and 60 ng per sample corresponding to 0.3 and 6.0 ng methadone exhaled in breath per min. The correlation coefficients (r2) of the calibration curves were between 0.991 and 0.999 (mean 0.996, n=5)

TABLE 2

Summary of data obtained for methadone sampled in exhaled breath from 13 methadone maintenance patients.

| Case no. | Number of breaths | Methadone dose (mg/d) | Sampling time after dose intake (min) | Mouth wash prior to sampling | Methadone excretion (ng/min) |
|---|---|---|---|---|---|
| 1 | 90 | 41 | 13 | No | 1.0 |
| 2 | 100 | 59 | 44 | Yes | 0.39 |
| 3 | 100 | 127 | 27 | No | 1.9 |
| 4 | 140 | 91 | 10 | Yes | 5.8 |
| 5 | 80 | 94 | 25 | Yes | 1.2 |
| 6 | 155 | 45 | 10 | Yes | 0.87 |
| 7 | 100 | 42 | 60 | Yes | 3.5 |
| 8 | 100 | 56 | 13 | Yes | 1.5 |
| 9 | 120 | 35 | >10[a] | No | 1.4 |
| 10 | 70 | 46 | 12 | Yes | 0.90 |
| 11 | 100 | 66 | 13 | Yes | 0.93 |
| 12 | 100 | 90 | 18 | Yes | >6.0[b] |
| 13 | 120 | 59 | 8 | Yes | 2.6 |

[a]Not noted
[b]Extrapoled value from 180 ng/disc standard was 78

LOD (signal to noise 3) was estimated to 4 pg/sample (~0.4 pg in breath/min) and LLOQ (signal to noise 10) was estimated to 15 pg/sample, while the calibrated measuring range was 3.0-60 ng/sample. Imprecision (coefficient of variation, CV) was estimated within series to 1.6%, 1.9% and 2.0% at levels 3.0, 15, and 45 ng/sample (n=6). The accuracy was 104%, 109% and 104%, respectively. The extraction recovery of methadone from the Empore disc surface was measured in duplicate using samples at the 15 ng/sample level and was 96.6% (n=4). Matrix effects were estimated by addition of methadone (15 ng/sample) to extracts prepared from blank Empore discs and from Empore discs used for collection of exhaled breath from a healthy volunteer. The methadone peak area was compared with the reference sample containing no matrix. The matrix effect for blank Empore discs was 109% (SD 9, n=8) and for breath sample discs 108% (SD 40, n=8).

Application of the method: Methadone was detected in the sampled exhaled breath from all 13 studied patients, which was in accordance with the daily observed dose intake of methadone (Table 2). In all cases this was also supported by compliance to treatment as controlled by routine analysis of urine and by supervised dose intake. None of the 10 control subjects had detectable levels of methadone (<0.005 ng/min) in the exhaled breath samples. The detection level was set by the contribution of methadone-d3 to the two methadone channels.

Identification of detected methadone was based on a correct relative (to methadone-d3) retention time (±0.5%) and correct (<±20%) relative ion intensity ratio between the two product ions. The amount of methadone collected from breath was high enough to produce strong analytical response. This makes the identification secure and methadone was identified according to these criteria in samples from all methadone patients. The amount of methadone ranged >15-fold from 0.39 to >6.0 (78) ng/min. The highest value obtained was outside the measuring range and appeared to be an outlier. Table 2 summarizes the results and collected data for the 13 patient samples. No difference in results could be observed between subjects sampled with or without mouth wash prior to sampling (Table 2). No significant correlation of excretion rate with methadone dose was observed.

Each subject was breathing at own chosen pace. The number of breaths during the 10 min sampling time was therefore recorded (Table 2). Table 2 also reports the actual sampling time after dose intake. Due to practical reasons this time interval could not be the same for all subjects but varied between 8 and 60 min.

The Empore discs are commercially available, for instance from 3M Inc. These products are made of bonded silica. They are conventionally intended for use for the solid phase extraction of liquid analytes, which usually are highly diluted. It was hitherto not known to use such collective elements as a filter discs for collecting non-volatile or volatile compounds of substances in a gas, such as exhaled breath. Present applicants have realized this unexpected potential and above example shows the feasibility of that inventive use. As pressure drop through the commercially Empore discs is high, some embodiments are provided with the aforementioned pump assisted breathing through the discs. Alternatively, or in addition, the discs may be modified to reduce pressure drop over them. This may be done by pinching holes through a portion of the surface of the disc. Alternatively, or in addition, an Empore disc is hold in place by spacer pieces, as described above.

A variety of functional groups, such as octadecyl (C18) and octyl (C8) can be bonded to the silica surface to provide non polar interactions.

Each of these sorbents exhibits unique properties of retention and selectivity. This is based on the fact that drug compounds are lipophilic as such because they can pass the blood-brain barrier. The sorbents, such as C18, render the silica surface lipophilic. Therefore, these collective elements provide for selectivity for a particular analyte, such as for a specific drug substance.

The choice of which sorbent is best for a particular method will be influenced by the percent recovery of analyte from the sample matrix and the cleanliness of the resulting chromatography.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A portable system configured to collect a sample of non-volatile compounds from exhaled breath of a subject, said system comprising:
   a housing made from two parts, a first part and a second part, being joined together to define an interior space, wherein the first part comprises an inlet for said subject to exhale into said housing and the second part comprises an outlet for said exhaled breath to exit through;
   a sampling unit arranged transversely across said interior space by being attached to walls of said housing and dividing the interior space to form a first chamber within said first part wherein exhaled breath is received through the inlet thereby forcing exhaled breath flowing from said inlet to said outlet to pass through said sampling unit,
   wherein said sampling unit comprises an electrostatic nonwoven polymeric fibrous web filter membrane, wherein said filter membrane is adapted to collect non-volatile compounds, carried by aerosols, from said exhaled breath from said subject; and wherein said non-volatile compound is extractable from said filter membrane using a solvent for analysis with liquid chromatography-mass-spectroscopy;
   a detachable mouthpiece element connectable to said inlet; and
   a flow sensor arranged at said detachable mouthpiece and being configured to determine flow of exhaled breath through the housing;
   wherein said sampling unit is removably disposed in said housing with a collecting element disposed therein, and wherein said system consists essentially of said first part with the detachable mouthpiece and flow sensor, said second part with said outlet and said sampling unit, and wherein said outlet is sized to form substantially the whole back of the second part of the housing.

2. The system according to claim 1, comprising a pump, wherein said pump is arranged downstream of said sampling unit.

3. The system according to claim 1, wherein said housing and sampling unit are configured to provide a pressure drop through said system, when said subject exhales into the inlet, of not higher than 2 cm water.

4. The system according to claim 1, wherein said filter membrane has a mesh size to collect particles from said exhaled breath with a size of 0.2-0.7 μm.

5. The system according to claim 1, wherein said filter membrane is configured such that a pressure drop of less than 2 cm water occurs between said inlet and outlet at an exhalation flow rate of about 0-9 liter/min.

6. The system according to claim 1, wherein said filter membrane comprises at least two filter membranes configured to discriminate between at least two different drug substances.

7. The system according to claim 1, wherein a compartment for collecting at least one of saliva or condensate is disposed between said inlet and said sampling unit and/or after said sampling unit and said outlet.

8. The system according to claim 1, wherein said at least one non-volatile compound is at least one drug substance in said exhaled breath that can pass from the subject's blood via the lung membrane.

9. The system according to claim 8, wherein said drug substance comprises at least one of Amphetamine, ecstasy, *Cannabis*, THC and cannabinoids, Opiates, heroin, morphine, 6-AM, Cocaine, Benzodiazepines, Propoxyphene, Methadone, Buprenorphine, Tramadol, LSD, Designer/Internet drugs, Kathinon, GHB, Meprobamat, Z-drugs, Tryptamines or, Anabolic steroids.

10. The system of claim 1, wherein said filter membrane comprises a layered filter membrane with at least a first layer and a second layer, wherein said first layer is a gas permeable layer and said second layer is adapted to collect said sample.

11. The system of claim 10, wherein said filter membrane second layer comprises a layer comprising the nonwoven polymeric fibrous web.

12. A method for portably collecting a sample from exhaled breath of a subject, and for detecting the presence or determining the quantitative amount of at least one non-volatile compound carried by aerosols from a lung in said exhaled breath, said method comprising:
   collecting said sample comprising at least one non-volatile compound from said subject using a system comprising a housing made from two parts, a first part and a second part, being joined to define an interior space with an inlet for exhaling into said housing and an outlet for said exhaled breath to exit through, a sampling unit arranged transversely across said interior space by being attached to walls of said housing to form a first chamber into which exhaled breath is received through the inlet, thereby forcing exhaled breath flowing from said inlet to said outlet to pass through said sampling unit, wherein said sampling unit comprises an electrostatic nonwoven polymeric fibrous web filter membrane, wherein said filter membrane is adapted to collect at least one non-volatile compound of said at least one drug substance from said exhaled breath from said subject, said system unit further comprises a detachable mouthpiece connectable to said inlet; and a flow sensor arranged at said detachable mouthpiece configured to determine flow of exhaled breath through said housing; and wherein said sampling unit is removably disposed in said housing with a collecting element disposed therein, and wherein said system consists essentially of said first part with the detachable mouthpiece and flow sensor, said second part with said outlet and said sampling unit, and wherein said outlet is sized to form substantially the whole back of the second part of the housing;
   extracting said at least one non-volatile compound from said filter membrane using a solvent comprising methanol; and
   analyzing said extracted at least one non-volatile compound using liquid chromatography-mass-spectroscopy or Surface Enhanced Ra man Spectroscopy.

13. The method according to claim 12, comprising generating suction by means of a pump arranged downstream of said sampling unit.

14. The method according to claim 13, wherein said suction is assisting said subject to pass said exhaled breath through said sampling unit.

15. The method according to claim 12, wherein a flow of said exhaled breath is generating a pressure drop not higher than 2 cm water over said sampling unit.

16. The method according to claim 12, comprising collecting of saliva or condensate from said exhaled breath using a compartment arranged between said at least one inlet and said sampling unit and/or after said sampling unit and said outlet.

17. The method according to claim 12, comprising discriminating between at least two different drug substances by means of at least two collecting elements.

18. The method according to claim 12, further comprising collecting said sample by means of a filter membrane having a mesh size of 0.2-0.7 μm.

19. The method according to claim 18, further comprising collecting said sample by means of a filter membrane having a pressure drop of less than 2 cm water occurring between said inlet and outlet at an exhalation flow rate of about 0-9 liter/min.

20. The method according to claim 12, wherein said at least one non-volatile compound of said at least one drug substance in said exhaled breath are compounds that can pass from the subject's blood via the lung membrane.

21. The method according to claim 12, wherein said drug substance comprises at least one of Amphetamine, ecstasy, *Cannabis*, THC and cannabinoids, Opiates, heroin, morphine, 6-AM, Cocaine, Benzodiazepines, Propoxyphene, Methadone, Buprenorphine, Tramadol, LSD, Designer/Internet drugs, Kathinon, GHB, Meprobamat, Z-drugs, Tryptamines, or Anabolic steroids.

22. The method according to claim 12, wherein said method comprises non-intrusive breath testing of a subject for drug substances.

23. The method of claim 22, further comprising performing said testing of said subject without sampling blood or urine.

24. A portable system configured to collect a sample of non-volatile compounds from exhaled breath of a subject, said system comprising:
  a portable, hand-held housing made from two parts, a first part and a second part, being joined together to define an interior space with an inlet for said subject to exhale into said housing and an outlet for said exhaled breath to exit through;
  a removable sampling unit disposed in the housing comprising an electrostatic nonwoven polymeric fibrous web filter membrane configured and specifically adapted to collect non-volatile compounds carried by aerosols having a particle size of 0.2-0.7 μm in exhaled breath, said sampling unit further being configured and specifically adapted for extraction of said non-volatile compound from said filter membrane using a solvent for analysis with liquid chromatography-mass-spectroscopy;
  a detachable mouthpiece element connectable to said inlet; and
  a flow sensor arranged at said detachable mouthpiece configured to determine flow of exhaled breath through the housing;
  wherein said removable sampling unit is arranged transversely a cross said interior space by being attached to walls of said housing and dividing the interior space to form a first chamber wherein exhaled breath is received through the inlet thereby forcing exhaled breath flowing from said inlet to said outlet to pass through said sampling unit;
  wherein said housing, said sampling unit and said filter membrane are configured to provide a substantially straight flow path for exhaled breath from said detachable mouthpiece through the outlet with a back pressure, when said subject exhales into the inlet, of not higher than about 2 cm water at an exhalation flow rate of about 0-9 liter/min; and
  wherein said system consists essentially of said first part with the inlet, the detachable mouthpiece and flow sensor, said second part with said outlet and said sampling unit, and wherein said outlet is sized to form substantially the whole back of the second part of the housing.

* * * * *